United States Patent [19]
Haggett et al.

[11] Patent Number: 5,973,774
[45] Date of Patent: Oct. 26, 1999

[54] PORTABLE INSTRUMENT TO DETERMINE CONCENTRATION OF AFFF IN FRESH AND SEA WATER SOLUTIONS

[75] Inventors: Randall D. Haggett, Dartmouth; Richard D. Dittman, Hatchett Lake, both of Canada

[73] Assignee: Her Majesty the Queen in right of Canada, as represented by the Minister of National Defence of Her Majesty's Canadian Government, Ottawa, Canada

[21] Appl. No.: 09/056,821

[22] Filed: Apr. 8, 1998

[51] Int. Cl.[6] ..................................................... G01B 9/00
[52] U.S. Cl. ........................... 356/135; 356/133; 356/128
[58] Field of Search .................................. 356/128, 133, 356/135, 134

[56] References Cited

U.S. PATENT DOCUMENTS

| | | | |
|---|---|---|---|
| 3,932,038 | 1/1976 | Schweizer et al. | 356/135 |
| 4,692,024 | 9/1987 | Bloss | 356/135 |
| 4,749,274 | 6/1988 | Aoki et al. | |
| 5,048,952 | 9/1991 | Miyata et al. | 356/135 |
| 5,565,978 | 10/1996 | Okubo et al. | |

*Primary Examiner*—Robert Kim
*Assistant Examiner*—Reginald A. Ratliff
*Attorney, Agent, or Firm*—Larson & Taylor

[57] ABSTRACT

A compact portable instrument for determining the percentage concentration of a material in a solution such as the amount of concentrate in an output from an Aqueous Film Forming Foam generator used to extinguish fires. The instrument comprises a refractive index sensor with a reflective type refractometer prism having a measuring surface in contact with liquids placed in a sample holder formed by an opening through a retainer plate. The measuring surface of the prism covers that opening and presses the retainer plate towards an outer surface of the instrument, that outer surface having entrance and exit ports for sample liquids at that opening. The refractometer senses the refractive index of liquid in the sample holder and, when properly calibrated, provides an output to a digital display that directly indicates the percentage concentration of material in the liquid. A small thin sample size of about 100 microliters provides rapid thermal stabilization of the sample liquid and allows the percentage concentration to be quickly and accurately determined.

20 Claims, 9 Drawing Sheets

PORTABLE INSTRUMENT TO DETERMINE CONCENTRATION OF AFFF IN FRESH AND SEA WATER SOLUTIONS

FIELD OF THE INVENTION

The invention relates to an instrument for determining the concentration of a material in a liquid solution and in particular to a compact portable instrument with a refractive index sensor that can detect small refractive index variations in liquids and, from those, determine the percentage concentration in that solution with a high degree of precision.

BACKGROUND OF THE INVENTION

An aqueous solution containing a surfactant known as Aqueous Film Forming Foam (AFFF) is often required when fighting fires of flammable liquid fuel. That foam forms an air-excluding vapour-suppressing aqueous film on the surface of the fuel. This foam is generated by pumping a concentrated solution of AFFF from reservoir tanks through a foam/liquid proportioner where it is mixed with water, either fresh or seawater, in a particular ratio. It is important that correct proportioning is maintained in making a foam that has a proper expansion to form a fire-resistant foam. If proper proportioning is not maintained, then the resulting foam may be ineffective in fighting a fire or more AFFF concentrate than actually required may be used. If more concentrate than required is used, then this would shorten the time before the amount of AFFF concentrate in the reservoirs is exhausted which reduces the effective fire fighting time.

Several methods are currently used to determine the concentrating of AFFF from the foam/liquid proportioner discharge. One method is by using a conductivity meter. However, differences in temperature may change conductivity of the solution. Thus, careful calibration and temperature compensation procedures are required for most of these meters. Furthermore, conductivity meters cannot be used when seawater is used for generating the fire fighting foam due to the conductivity that is already present in sea water.

On navy ships, the capability to effectively fight on-board fires caused by flammable liquids such as aviation turbine fuel, naval distillate fuel, lubricating oils and hydraulic fluids is provided through the use of AFFF concentrate. That AFFF concentrate is pumped, from reservoirs for the concentrate, through a foam/liquid proportioner where it is mixed with sea water in a predetermined ratio by injecting a metered amount of concentrate into the discharge stream from the foam/liquid pump. To generate an effective fire fighting foam, it is essential that the proper ratio of concentrate to sea water is maintained in the discharge from the pump.

A 6% foam solution is considered to be an optimum concentration for one type of AFFF to provide effective control of a liquid hydrocarbon fire. The resulting foam markedly increase the effective volume of the water and, by reducing the surface tension, the surfactant increases the ability of the water to wet other surfaces instead of beading. If the concentration of AFFF in the pump discharge drops below 6%, the ability of the foam to smother a fire is greatly reduced while the concentrate is used at an accelerated rate when the ratio raises above 6%. That accelerated rate will shorten the length of time before the supply of concentrate in their reservoirs is exhausted. This could create a serious problem on ships where a new supply of AFFF may not be readily available for a lengthy period of time. Therefore, it is essential to be able to determine the concentration of the liquid solution at a pump's discharge in order to provide proper adjustment of the foam/liquid proportioner and obtain an optimum fire fighting concentration in the discharge.

The use of a conductivity meter to determine the % concentration of AFFF at a pump's discharge is, as previously mentioned, not suitable when seawater is being used to generate the fire-fighting foam. Furthermore, naval proportioning systems are vulnerable to corrosion by seawater and are, as a result, the ones most in need of regular overhaul and monitoring. This frequently results in dockyard laboratories being requested to determine the concentration in the discharge from proportioning pumps when new pumps are installed or when pumps are overhauled or are being adjusted. One method that laboratories may use to determine the concentration is with a refractive index (RI) detector. This entails preparing varying standard sample solutions, ones containing 1, 2, 3, 4, 5, 6 and 7% AFFF by volume concentrations, with their refractive indexes being determined using a flow through refractive index detector. The refractive index for the samples, measured in millivolts (MV) at the detector's output, are recorded by a strip chart recorder to provide a visual representation of the instruments response to the samples. Those visual representations are then plotted against the solution concentration of the standard solutions in order to obtain calibration curves for the instrument. The response of the instrument to a sample from a pump's discharge is then measured and that response compared with the previously prepared calibration curve. The % concentration at the output from the pump can be determined from where the measured output of the RI detector to that sample fits on the calibration curve. This is a time consuming and expensive procedure since it can only be carried out with the required accuracy in a laboratory using large non-portable instruments. This poses a logistical problem for ships, in particular, as well as for many fire departments and air bases since it can take several days to obtain results from the laboratory as to the percentage of AFFF in the foam being generated at the output of the pump.

A very low refractive index is exhibited by these liquid solutions with only a very small change in the refractive index occurring with a change in concentration of AFFF solutions (0.005 RI units over a 0% to 9% range). Bench top refractive index detectors, such a described above, are capable of detecting a 1 part in $10^7$ change in refractive index which is suitable for determining the % concentration in a sample solution at the required resolution. Handheld manual prism refractometers have been used to measure the refractive index and determine the % concentration. These hand-held refractometers also require the user to plot the refractive indices of prepared standards and unknowns versus concentration to determine the AFFF concentration which is a time consuming process. Tests have determined that these refractometers can, at best, measure changes in refractive index in the order of 1 part in $10^3$ (versus 1 part in $10^7$ for a benchtop refractor) and this is insufficient sensitivity to detect the very small changes in refractive index necessary to determine the % concentration of AFFF solutions at the pump's discharge with the required accuracy.

SUMMARY OF THE INVENTION

It is an object of the present invention to provide a compact portable instrument to accurately determine, on site, the % concentration of material in a liquid solution with a precision that is substantially equal to that which can be achieved with large benchtop non-portable refractometers.

It is a further object of the present invention to provide a compact portable instrument to accurately determine, on site, the % concentrating of material in a liquid solution and to provide a direct readout display of that percentage.

A compact portable instrument according to the present invention for determining the percentage concentration of a material in a liquid solution, comprises a refractive index sensor with a reflective type refractometer prism having a measuring surface located so that the measuring surface contacts any liquid in a sample holder and wherein the measuring surface of said prism is adjacent an outer side of the instrument, which outer side contains an inlet port for samples of liquid solution and an outlet port for that liquid; the measuring surface being separated from said outer side by a retainer plate having an opening therethrough, which opening extends around an exit from and an entrance to the inlet and exit ports respectively, with that measuring surface covering one side of said opening and wherein a liquid impervious seal exists around that opening between the retainer plate and the measuring surface and between the retainer plate and said outer side to form said sample holder; the instrument having a substantially monochromatic light source located at an entrance window to said prism, the light source upon activation directing a light beam at an angle towards said measuring surface where a portion of said beam is reflected by the prism to a photodetector at an exit window of the prism, the portion of beam reflected to the photodetector being dependent on a boundary formed by critical angle $\phi_{CRIT}$ at said measuring surface, which angle is dependent on refractive indices of the prism and any liquid in contact with the measuring surface, and wherein the refractive index of a liquid solution in contact with the measuring surface is dependent on the percentage concentration of material in that liquid; an output from the photodetector being connected to the instrument's display unit via at least one amplifier having a gain such that the percentage concentration of a material in the liquid being sampled is directly displayed by the display unit.

A compact portable instrument according to a further embodiment of the present invention for determining the percentage concentration of a material in a liquid solution comprises a refractive index sensor with a reflective type refractometer prism having a measuring surface that forms one wall of a sample holder and wherein a substantially monochromatic light source, when activated, directs a conical beam of light into the prism and towards a portion of the measuring surface which contacts any liquid solution in the sample holder, the measuring surface reflecting a portion of the beam which is directed towards a photodetector, that portion being dependent on a boundary formed by a critical angle $\phi_{CRIT}$ at the measuring surface; the instrument having a support for the prism and a retainer plate with an opening therethrough, said support pressing the measuring surface of said prism towards said retainer plate to press said plate towards an outer panel of said instrument with a waterproof seal being formed around said opening between the retainer plate and outer panel and between the retainer plate and said measuring surface, the outer panel having an inlet port and an outlet port which are surrounded by said opening whereby a liquid solution can be inserted into that opening through the input port and removed from that opening via said exit port, the opening forming said sample holder for liquid solutions whose refractive index can be determined by the reflected portion of the said beam detected by said photodetector where the refractive index provides an indication of a percentage concentration by volume of a material forming part of the liquid solution in the sample holder and wherein said opening is oval shaped with the inlet port being located at one end of the oval and the exit port located at another end of said oval, an O-ring being snugly fitted in said opening and held in an oval shape by edges of that opening, the waterproof seal being formed by said O-ring being compressed between the measuring surface and outer panel by pressure exerted on said prism by said support.

A compact portable instrument according to a still further embodiment of the present invention for determining the percentage concentration of a material in a liquid solution comprises a refractive index sensor with a reflective type refractometer prism having a measuring surface that forms one wall of a sample holder and wherein a substantially monochromatic light source, when activated, directs a conical beam of light into the prism and towards a portion of the measuring surface which contacts any liquid solution in the sample holder, the measuring surface reflecting a portion of the beam which is directed towards a photodetector, that portion being dependent on a boundary formed by a critical angle $\phi_{CRIT}$ at the measuring surface; the instrument having a support for the prism and a retainer plate with an opening therethrough, said support pressing the measuring surface of said prism towards said retainer plate to press said plate towards an outer panel of said instrument with a waterproof seal being formed around said opening between the retainer plate and outer panel and between the retainer plate and said measuring surface, the outer panel having an inlet port and an outlet port which are surrounded by said opening whereby a liquid solution can be inserted into that opening through the input port and removed from that opening via said exit port, the opening forming said sample holder for liquid solutions whose refractive indices can be determined by the reflected portion of the said beam detected by said photodector, where the refractive index of any one liquid solution provides an indication of a percentage concentration by volume of a material forming part of the liquid solution in the sample holder and wherein said opening is oval shaped with the inlet port being located at one end of the oval and the exit port located at another end of said oval, an O-ring being snugly fitted in said opening and held in an oval shape by edges of that opening, the waterproof seal being formed by said O-ring being compressed between the measuring surface and outer panel by pressure exerted on said prism by said support and wherein an output from said photodetector is applied to at least one amplifier whose output is connected to a digital display panel, said at least one amplifier having a gain that is adjustable and, with proper calibration, allows the percentage concentration to be directly displayed by said display panel.

BRIEF DESCRIPTION OF THE DRAWINGS

The following detailed description of one embodiment of the present invention will be more readily understood when considered in conjunction with the accompanying drawings in which:

FIG. 7a is a top view of the retainer plate while

DESCRIPTION OF THE PREFERRED EMBODIMENT

Figure 1:
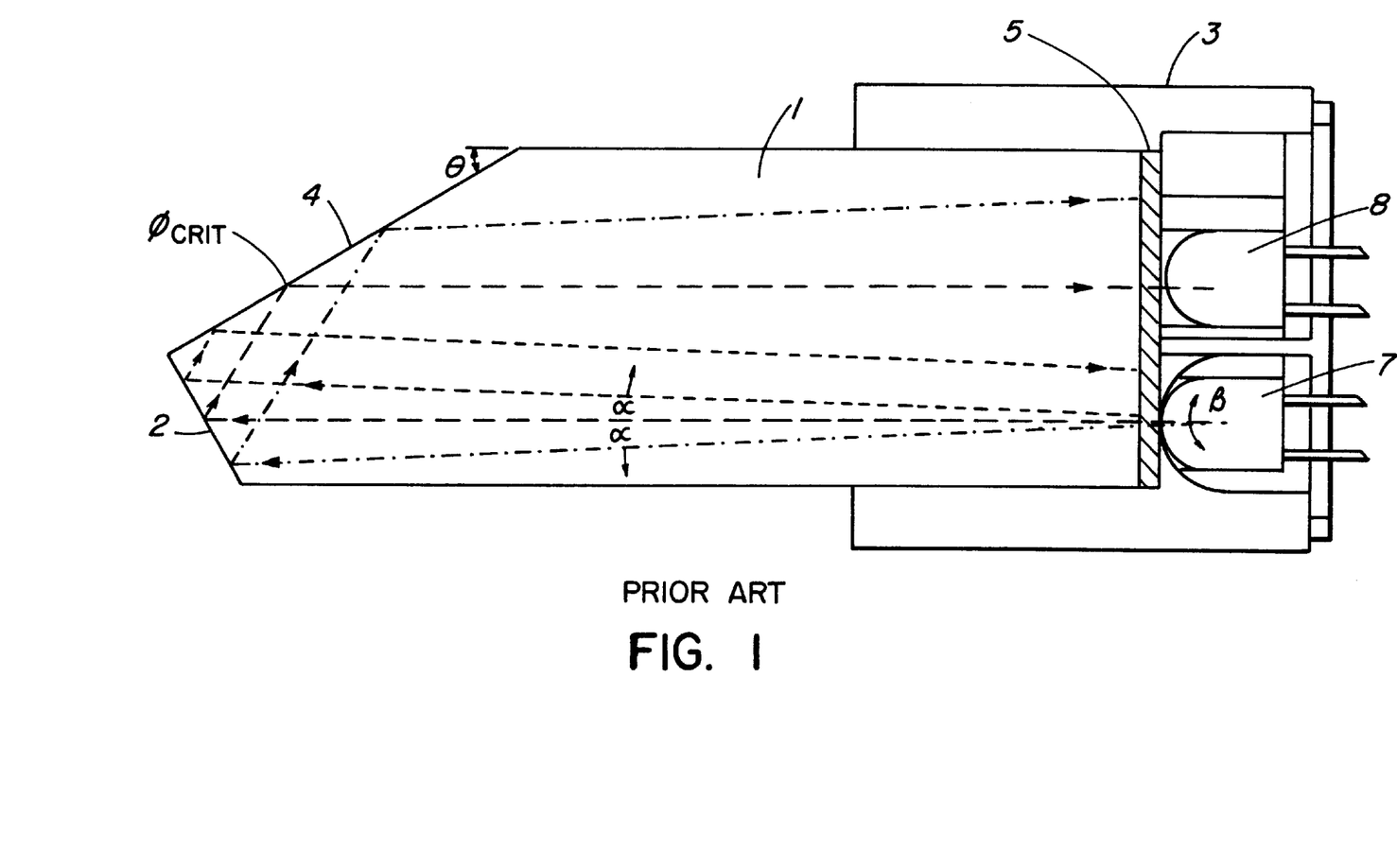
FIG. 1 is a cross-sectional view of one type of prior art prism and cap unit that could be used in an instrument according to the present invention.

Canadian Patent 2,054,887 by Richard D. Dittman illustrates one type of prism suitable for use in a refractometer such as in an instrument that performs a particular function as the type according to an embodiment of the present invention. This prism is shown in FIG. 1 along with cap unit 3 at the prism's entrance/exit window 5, the cap holding a light emitting diode (LED) 7 and light detector 8. The entrance/exit window 5 includes an optical bandpass filter for radiation emitted by LED7. The end of the prism 1 remote from entrance/exit window 5 has a polished planar surface 4 situated at an angle θ to the major axis of the prism, that axis being perpendicular to the window 5. The surface 4 serves as a measuring surface for the refractometer and is adapted to form an active interface with the liquid solution whose refractive index is to be measured. The angle θ=90° $\phi_{CRIT}$ where $\phi_{CRIT}$ is the critical angle limit of Snell's Law when the prism is immersed in water at room temperature. The prism has a planar reflecting surface 2 situated perpendicular to measuring surface 4 which is adapted to reflect the light beam emitted by LED 7 onto surface 4.

The LED 7 is preferably an infrared (GaAs) emitting diode with a narrow spectral emission peak at 930 nm which can be considered as nearly monochromatic. The use of monochromatic light avoids non-linear effects created by a band of frequencies. The LED 7 has a broad gaussian beam (≈±20°) dispersion so that light emitted from the LED is reflected by reflecting surface 2 onto the measuring surface 4. The portions of the light rays that are at angles larger than the critical angle are reflected by the surface 4 towards the photosensitive detector 8. Light rays incident on 4 at angles smaller that the critical angle refract in a sample solution in contact with surface 4 and are not reflected. Therefore, the refractive index of the sample solution can be determined by the amount of light from emitter 7 that is detected through a small aperture by detector 8.

The manual hand held prism refractometer currently approved by the National Fire Protection Association (NFPA) to determine % AFFF concentration can, at best, measure changes in refractive index in the order of 1 part in $10^3$. This gives them insufficient sensitivity to detect the change in refractive index with change in concentration of AFFF solutions (0.005 RI units over a 0% to 9% range) with the degree of precision required at present. The Portable Handheld Aqueous Suppressant Analysing Refractometer (PHASAR) according to the present invention and illustrated in FIGS. 2 to 5 is capable of detecting a 1 part in $10^9$ change in refractive index making it six orders of magnitude more sensitive than the present handheld refractometers. This small handheld PHASAR is, as a result, able to accurately determine the concentration of AFFF in either fresh or sea water solutions to a resolution of 0.01 percent by volume.

Figure 2:
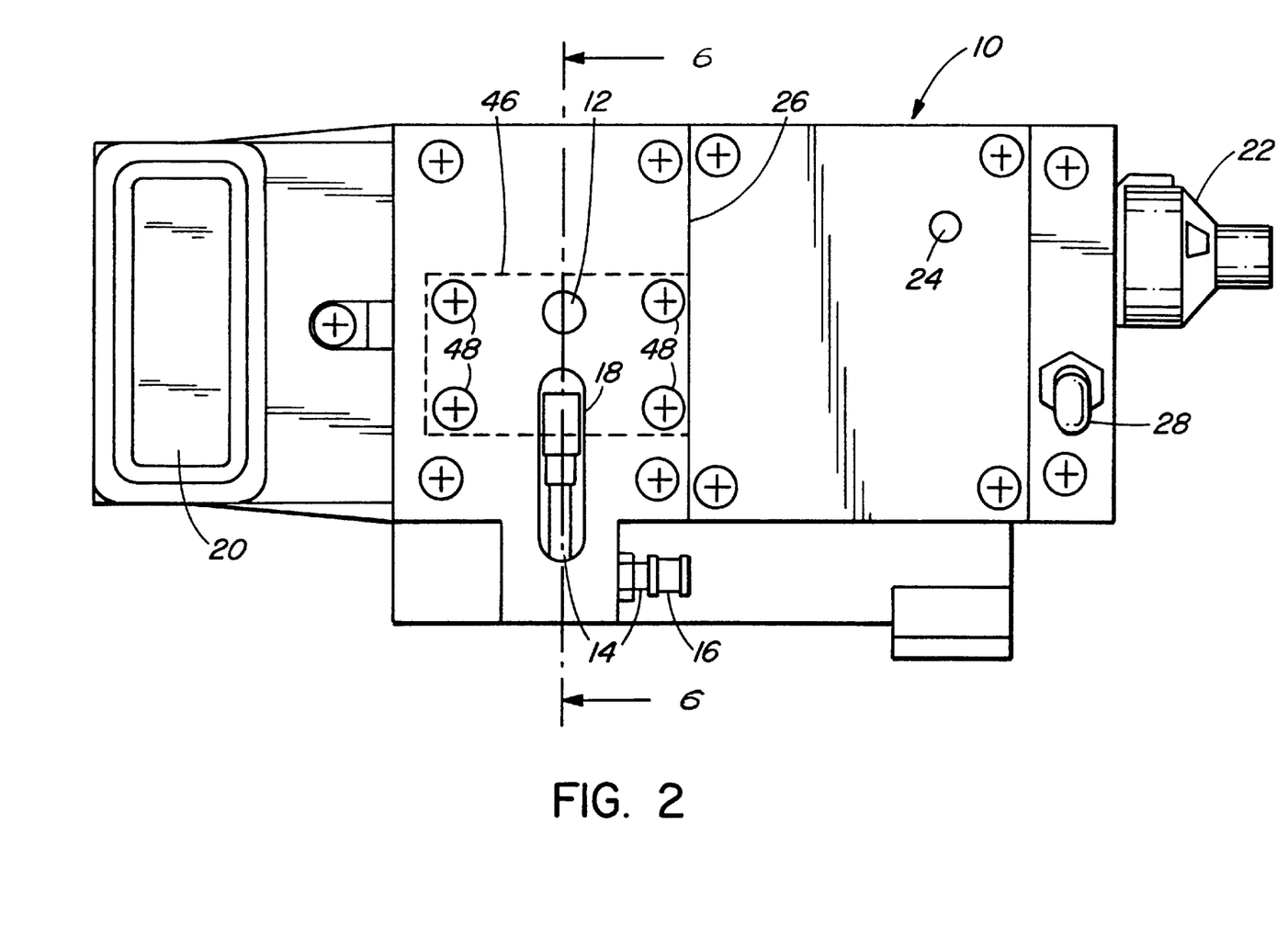
FIG. 2 is a top view of an instrument according to the present invention for determining the % concentration of material in a liquid solution, the prism holder being shown in dotted lines.
Figure 3:
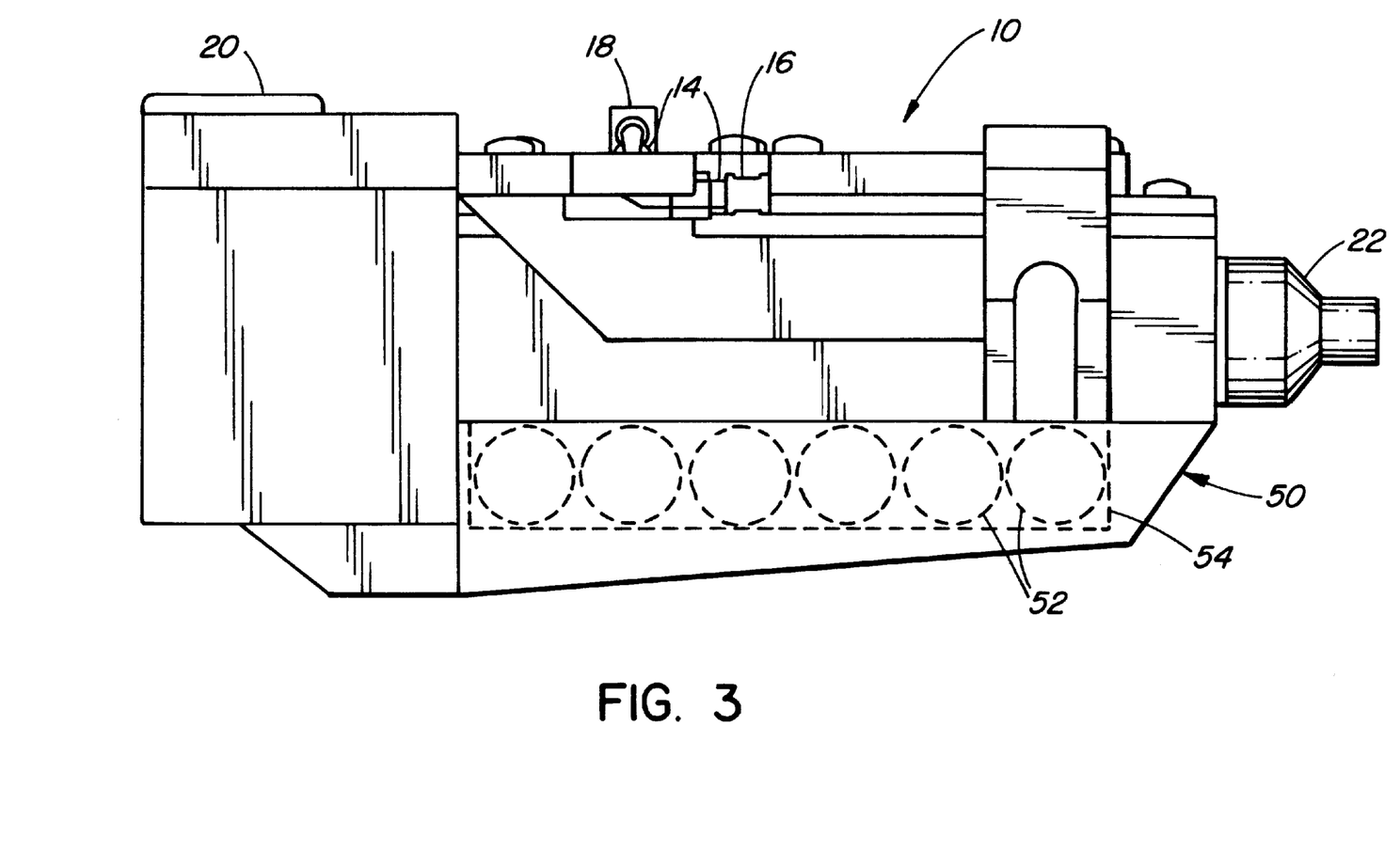
FIG. 3 is a side view of the instrument shown in FIG. 1.
Figure 5:
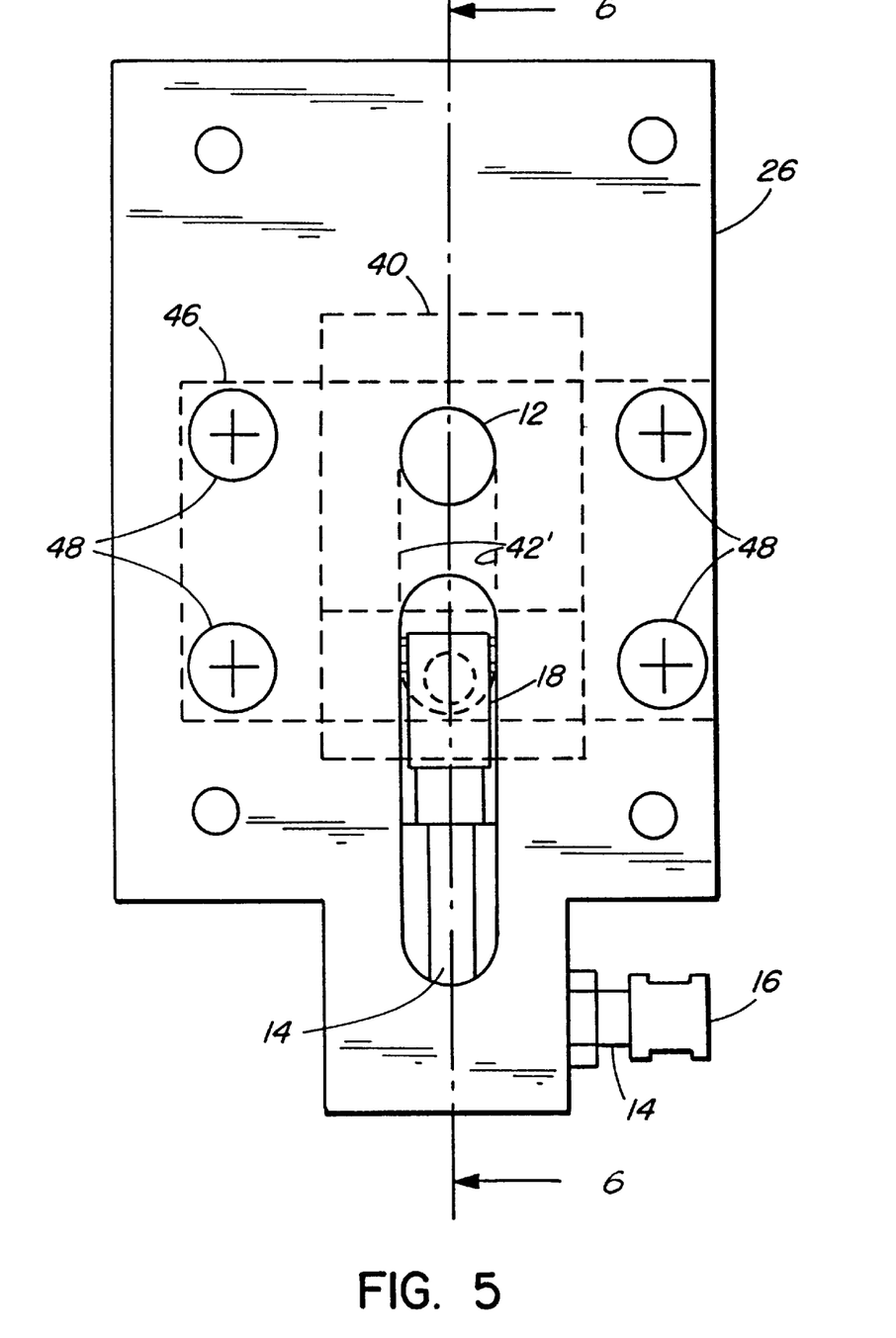
FIG. 5 is an enlarged top view of the sample inlet and exit portion of the instrument with an O-ring retainer plate for the sample holder being shown in dotted lines.
Figure 6:
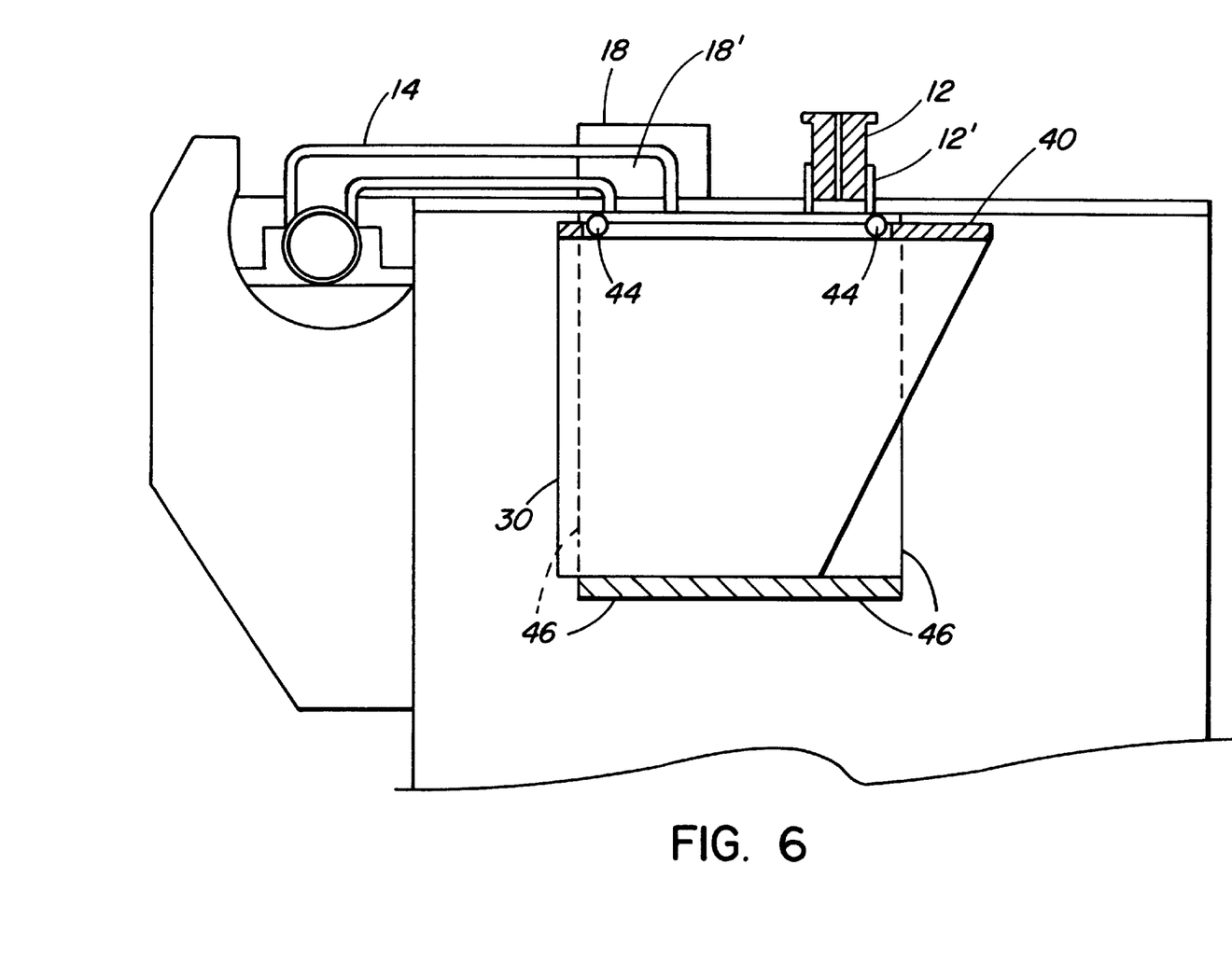
FIG. 6 is a cross-sectional view along Section A—A of FIGS. 2 and 5.

The main features of the Portable Handheld Aqueous Suppressant Analysing Refractometer (PHASAR) are best illustrated in the top view of FIG. 2, the side view of FIG. 3 and the enlarged cross-sectional view of FIG. 6 taken along Section A—A of FIG. 2 and enlarged top central panel view of FIG. 5. The top view of PHASAR 10 in FIG. 2 shows a digital display panel 20 at the left side (rear end) of the PHASAR which provides a direct readout of the percentage concentration of AFFF in a sample liquid solution injected into the instrument. The central panel 26 of the top view in FIG. 2 contains a centrally located sample inlet formed by a septum 12 of compressible plastic material fixed in an inlet port through which a liquid sample solution can be inserted by a hypodermic syringe (not shown). An exit port, located on the same cross-sectional line A—A as inlet 12, is spaced a short distance from inlet septum 12 and extends up through an upwardly extending protrusion 18. A tube 14 is connected to an output from protrusion 18 and extends to an output closed by a further septum 16 through which a disposal hypodermic syringe (not shown) is inserted. The use of two hypodermic syringes, at the inlet septum 12 and outlet 16, results in increased pressure on the liquid solution sample in the instrument (up to 50 psi) due to compression of air created in the disposal syringe as the sample liquid is inserted, forced through a sample holder and out into the disposal syringe. This pressure tends to prevent bubbles forming at the sample area. Bubbles that might occur in the sample area would interfere with any measurements made. However, bubbles tend to raise in a liquid. Therefore, the pressure exerted by air compressed in the disposal syringe would tend to force any bubbles that might be created out through the input septum 12 once the hypodermic syringe containing the sample liquid is removed from septum 12. Alternatively, the outlet tube 14 can be extended and flow into a disposal container for the samples. This alternative approach creates a flow-through refractometer that can be used for continuous sampling of the concentration of material in various types of mixtures or solutions. The side view of PHASAR in FIG. 3 shows the upwardly extending protrusion 18 that forms an outlet port and the connected outlet tube 14 along with the location of outlet septum 16 in more detail.

The top view of the PHASAR shown in FIG. 2 illustrates, in addition, the location of an ON-OFF switch 28 near the front of the instrument, a zero adjustment potentiometer 22 located on the front surface (also shown in FIG. 3 and 4) and a battery LOW indicator light 24. The batteries 52 are located in container 54 at a lower portion 50 of the PHASAR as shown in the side view of FIG. 3, container 54 and batteries 52 being indicated by dotted lines. The batteries 52 (six Ni-Cad) can be recharged by a connector (not shown) located in the rear of instrument 10 when light 24 indicates that they require recharging.

FIG. 5 is an enlarged view of center panel 26 that forms part of the top surface of the instrument, the inlet port (septum 12) and outlet 18 for sample solutions being located on panel 26. The position of prism holder 46 inside of the instrument along with the position of an O-ring retainer plate 40 are shown in dotted lines in FIG. 5.

Figure 7A:
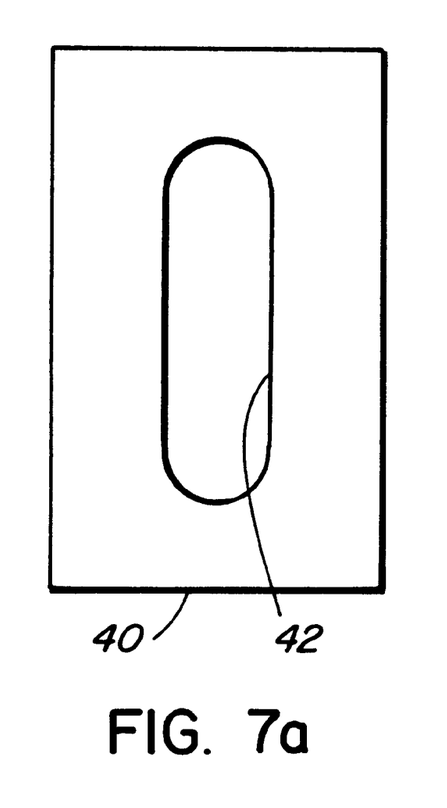
Figure 7B:
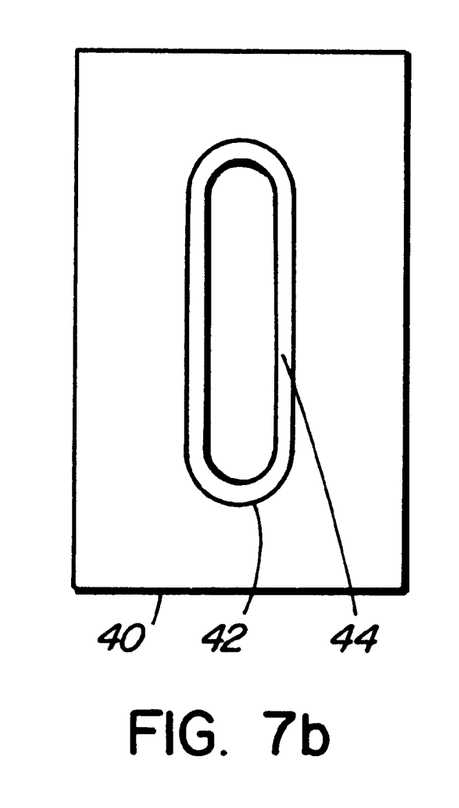
FIG. 7b shows the retainer plate with an O-ring in an oval opening through that plate to form a sample holder.

The cross-sectional view of FIG. 6 along Section A—A of FIGS. 2 and 5 illustrates the placement of the prism 30 and retainer plate 40 for a liquid sample inside the instrument to form a liquid sample holding cavity at the measuring surface of prism 30. The retainer plate as shown in FIG. 7a has an oval shaped opening 42 which extends through plate 40 and in which an O-ring 44 (size 2015 in this instrument) fits so that it is held in an oval shape as illustrated in FIG. 7b. The O-ring retainer plate, with the O-ring in place, is positioned beneath upper panel 26 with the outer ends of the O-ring oval extending around the outer portions of the inlet and outlet ports so that those ports are entirely located inside the oval shape of the O-ring. This is illustrated by dotted lines 42' in FIG. 5. The measuring window of prism 30 is positioned next to retaining plate 40 and clamped in position. In this particular embodiment, the prism is supported inside the instrument by a U-shaped polyethylene clamp 46, the bottom of which is shown in cross section in FIG. 6. The clamp is held in position by four screws 48 which extend through of top of center panel 26 into the top ends of the U shaped clamp. That clamp causes the prism to compress the O-ring 44 between the measuring surface 32 (see FIG. 8*b*) of prism 30 and the upper panel 26 forming a seal around the sample holder cavity inside the oval shaped O-ring. The measuring surface 32 of the prism completely surrounds the O-ring with the space inside the O-ring forming a holder for liquids whose refractive index are to be measured by the refractometer, the % concentration of a material in the liquid samples being determined from their refractive index. The retainer plate 40 and O-ring 44 forms a very small sample volume of about 100 microliters which is in contact with the measuring surface 32 of the prism and wherein the thickness of the sample is $\leq 1$ mm.

The temperature of sample solutions effects the refractive index of those solutions. The adverse temperature effects of the solutions on the refractive index, a problem with most refractometers, is overcome in the PHASAR by using the Black Body principal (thermal averaging) to provide temperature stabilization. In this PHASAR, the use of a very small sample volume (about 100 microliters or less) in relation to the large thermal mass of the instrument results in the sample temperature reaching a uniform temperature with that of the instrument in a very short time. The instrument utilizes the light source for the refractometer as a heat source with Newtonian heating providing a large thermal mass to average ambient temperature fluctuations in the sample. The stabilization of the average ambient temperature of the sample in the sample holder allows accurate measurements of the refractive index of the sample liquid to be made by the refractometer. The surface areas of the instrument, at least those areas in contact with or adjacent the sample holder and measuring area, are painted black to readily stabilize the temperature of the instrument with respect to the ambient surroundings.

One particularly unique feature of this design is the actual shape and thickness of the chamber that is formed when the prism 30 compresses the oblated O-ring 44 against the bottom of the central pad 26. This provides a sample chamber or manifold of about 100 microliters that is less than 1 mm thick. The thickness of the sample space formed ($\leq 1$ mm) acts to inhibit the formation of thermal vortices in the chamber. Those vortices or convection cells generally form in liquids when the bottom surface layer heats faster than the upper surface layer. Formation of such vortices result in the introduction of thermal noise in refractive index measurements and a deterioration in the accuracy obtainable The formation of convection cells is affected by the vertical thickness of the liquid layer, the temperature difference across the layer and its viscosity. Limiting the thickness and temperature difference decreases the chance that convection cells will form. In a refractometer the greatest rate of heating in the liquid would normally be expected to occur near the prism's surface since the infrared light from the source which passes through the interface is rapidly absorbed by the liquid. The sample layer is so thin in the sample chamber of the present invention that two traits prevent convection. The first is that the sample is so thin very little of the infrared is absorbed by the liquid. This results in the top of the sample chamber acting as an infrared absorbing surface and inverting the heating gradient. The second is that the viscosity of water is sufficiently large as to inhibit convection within thin layers.

Figure 8A:
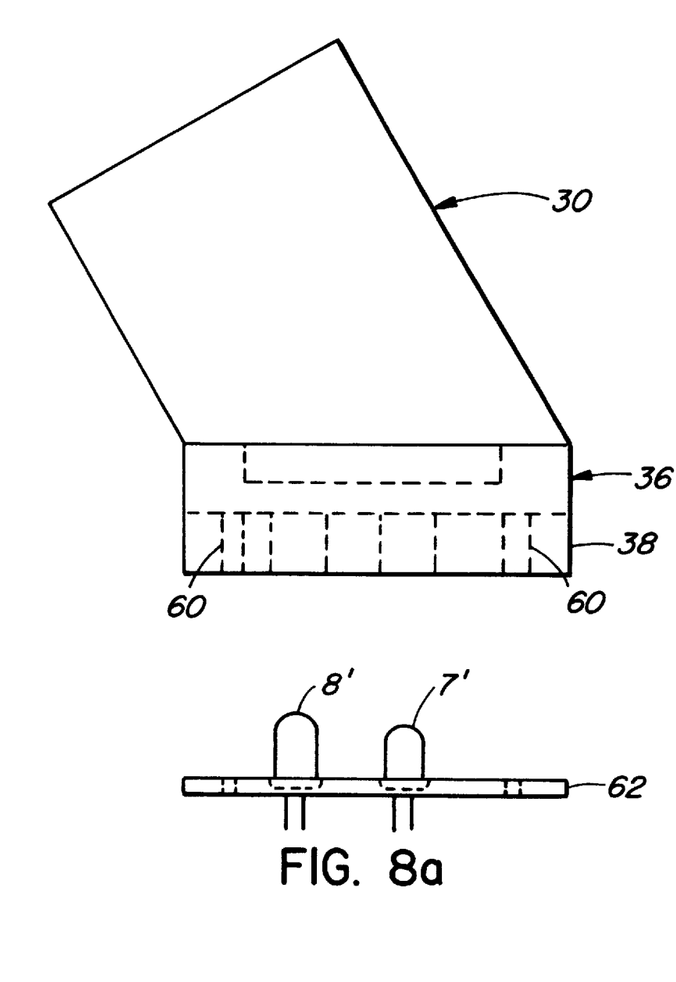
FIG. 8a is a cross-sectional side view of the prism for the instrument with the circuit board for the light emitter and detector separated from the prism and FIG. 8b is the same view showing the light emitter and detector installed at the base of the prism.
Figure 8B:
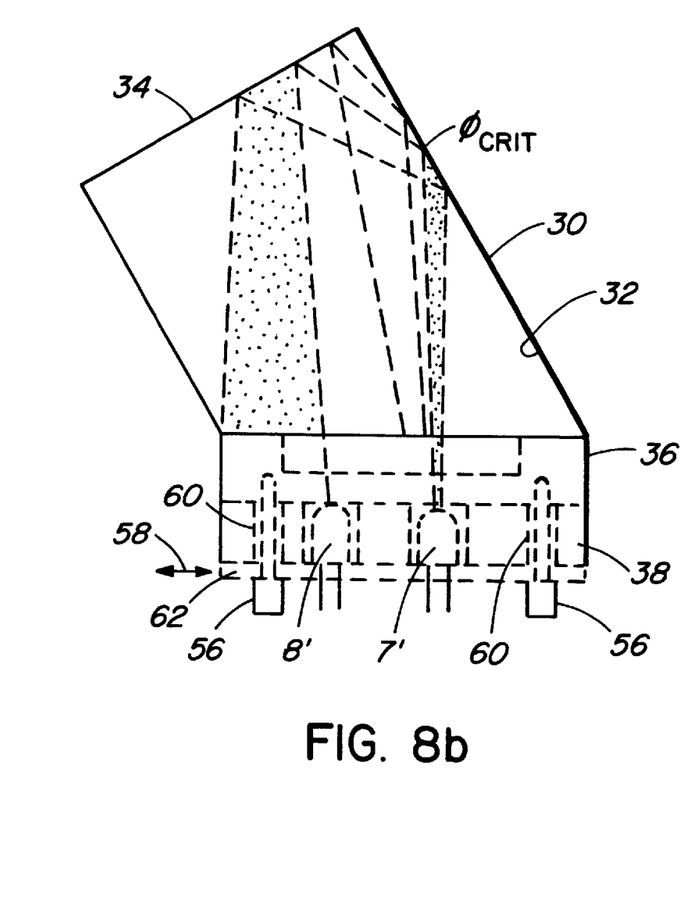

The prism 30 for the refractometer is shown in more detail in FIGS. 8*a* and 8*b*. In FIG. 8*a*, the LED 7' (an infrared source with a narrow peak at 930 nm), and photodetector 8' are mounted on a circuit board 62 which is shown as separated from an optical cap 38 that is to be attached to the prism's base 36. The base 36 has an entrance window to the prism which is at an angle to a measuring surface 32 on one side of the prism. That angle between the base and mirror is, in this instrument, approximately 61.0° when the prism is formed of an acrylic material. The measuring surface 32 of the prism is located at the long edge of the prism adjacent the base 36 and a reflecting mirror surface 34 is perpendicular to surface 32 at the end of the prism opposite base 36.

FIG. 8*b*, illustrates the prism when the LED 7+ and photodetector 8' are mounted in openings in optical cap 38 and held in position by guide pins or bolts 56 which extends through openings in circuit board 62, openings 60 in optical cap 38 and into threaded bores in base 36. The circuit board 62 is clamped into position with respect to the base by bolts 56 but the openings 60 through which the bolts 56 extend are slightly larger than the shafts of these bolts. This allows the circuit board 62 carrying LED 7' and detector 8' to be moveable in the direction of arrow 58 prior to bolts 56 being tightened to clamp circuit board 62 in position. That movement allows adjustment of the detector 8' with respect to the position of the critical angle $\phi_{CRIT}$ on measuring surface 34 to obtain an optimum gain and linearity adjustment for the refractometer.

The principles of operation for prism reflection type refractometers is well known and similar to that described in U.S. Pat. Nos. 4,749,274 (K. Aoki et al) or 5,565,978 (S. Okubo et al) and the previously mentioned Canadian Patent 2,054,887. Basically, a narrow bandwidth IR beam is emitted by LED 7' and and directed onto measuring surface 32 where some of the beam is reflected onto mirror surface 34 of the prism and back to the base 36. The beam from LED 7' has a broad dispersion angle ($\approx \pm 20°$) and rays from that beam which arrive at an angle to surface 32 that is larger the critical angle $\phi_{CRIT}$ will be reflected back by surface 32 and mirror surface 34 towards the base of the prism. Rays that arrive at an angle to surface 32 that is equal to or smaller than the critical angle $\phi_{CRIT}$ will be refracted out the prism away from the base. The beams reflected back to the base by mirror surface 34 can be detected by detector 8' and the critical angle determined by the amount of light detected by 8' i.e. the position of the critical angle $\phi_{CRIT}$ on surface 32. That critical angle is dependent on the refractive index of the prism and on the refractive index of material in contact with surface 32. Therefore, the refractive index of a liquid in contact with surface 32 can be determined from the light detected by detector 8' which has a narrow aperture so its field-of-view only covers a small area at the location on 32 of that critical angle where a boundary is formed between rays that are reflected back to the prisms base and the refracted rays. The position of detector 8' with respect to surface 34 can be adjusted by moving circuit board 62 in the direction of arrows 58 prior to clamping that circuit board in position in order to optimize the performance of the refractometers detector. Due to the small change in refractive index of various AFFF solutions, the change in position of the boundary between refracted and reflected rays is also very small.

Figure 4:
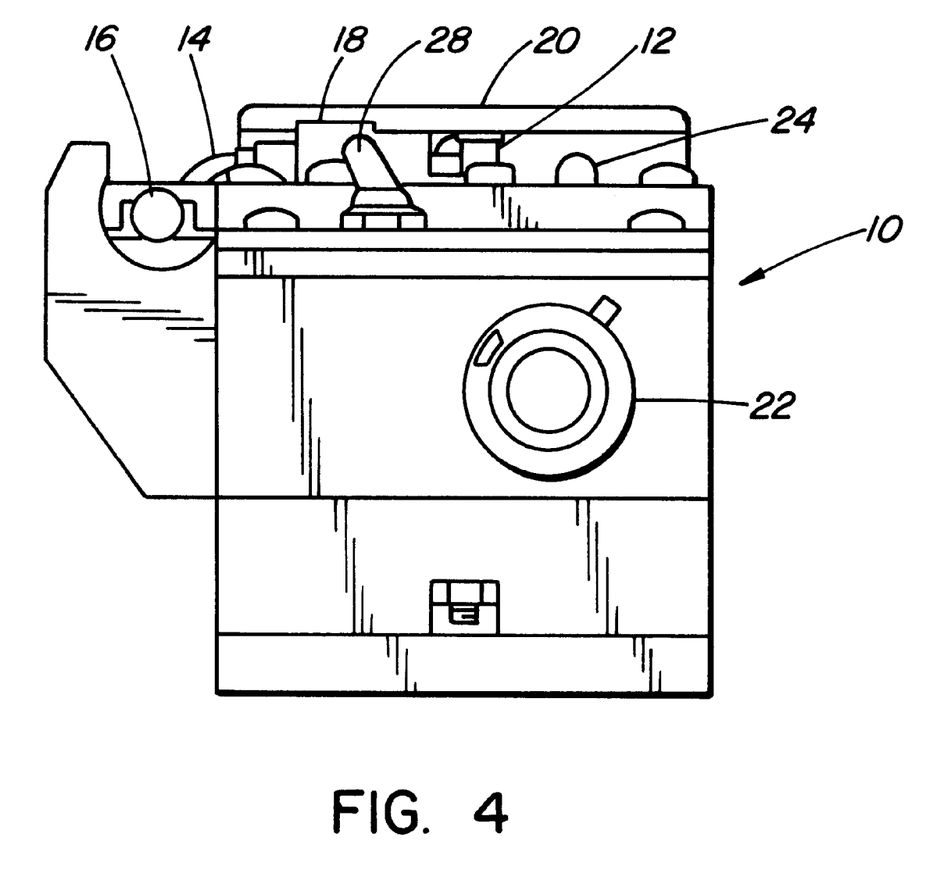
FIG. 4 is a front end view of the instrument shown in FIG. 1.
Figure 9:
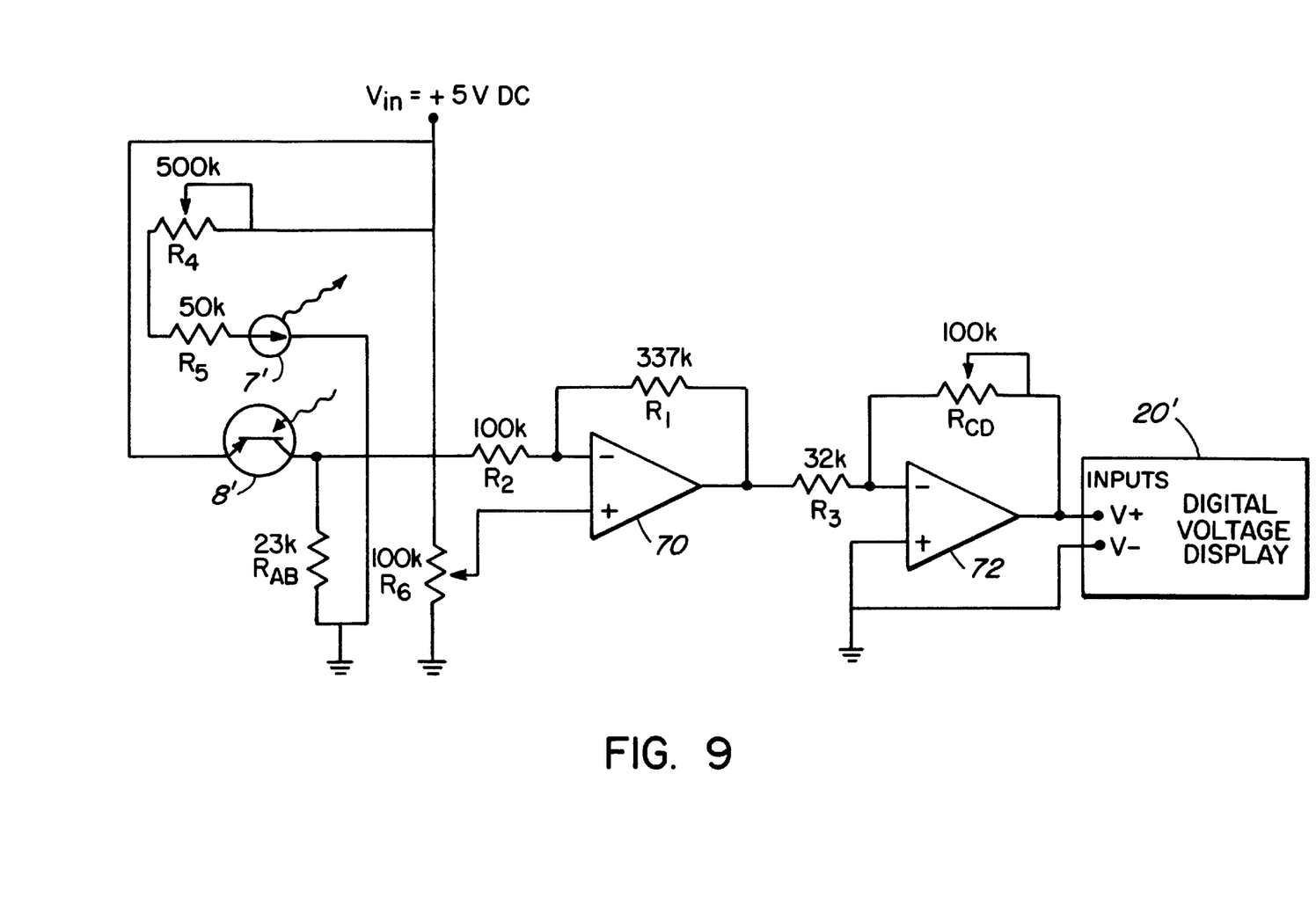
FIG. 9 is a circuit diagram for the instrument.

FIG. 9 is a circuit diagram for this instrument wherein the IR emitter 7' and detector 8' are supplied with power from a +5 VDC supply input. An OP 160 LED/detector pair obtainable from TRW Ltd. consisting of an OP 160 Infrared LED (peak emission 930 nm) and an OP 500 photo transistor are suitable for emitter 7' and detector 8'. The output from photo transistor 8' is applied to an input of a Dual Op Amp consisting of a first OP Amp 70 (LM 358 1/2) whose output is connected to an input of a second Op Amp 72 (LM 358 2/2). A suitable Dual Low Power Op Amp is LM 358 obtainable from Motorola Inc. The output from Op Amp 72 is connected to a digital voltage display unit 20' (display panel 20 in FIG. 2) with a potentiometer $R_{CD}$ between the input and output of Op Amp 72 being used to adjust the gain and compensate for thin film fouling of the prism. $R_{CD}$ is adjusted by a set screw (not shown) on a side of the instrument which, on this particular instrument, was the side opposite to the one shown in FIG. 3, the set screw being located near the front top surface. The potentiometer $R_6$ to the + input of the Op Amp 70 provides a linear offset control that is used for salinity and temperature compensation. $R_6$, via its control dial 22, is used when a reference liquid, i.e. fresh water or sea water, is used to provide an initial "0" setting for the instrument. The potentiometer $R_6$ is adjusted by potentiometer dial 22 located on the front of the instrument as shown in FIGS. 2, 3 and 4 to obtain a "O" setting on the digital display 20'.

To measure the concentrating of AFFF in an output from a foam discharge pump a sample of that output is obtained. If the AFFF concentrate is being mixed with seawater, then a sample of the seawater (without any concentrate in it) is injected into the instrument via a hypodermic needle inserted into septum 12 and the instrument activated by switch 28. Once the instrument has been stabilized after being switched ON, the potentiometer 22 is adjusted to set the digital display 20 to 00.000% for the refractive index associated with that seawater. If fresh water was being mixed with the AFFF concentrate, then the instrument would be adjusted to a zero setting using that fresh water in the sample holder.

Once a zero setting for the instrument is obtained, using fresh or seawater samples as above, that first sample is withdrawn from the sample holder. In this case, the plunger of the disposal syringe in output 16 is withdrawn to withdraw liquid from the sample holder formed by O-ring 44. Next a sample of liquid to be measured is inserted in the sample holder by an hypodermic needle through septum 12. The % concentration of AFFF in the sample is obtained by the prism measuring the refractive index, and that % is directly displayed on the digital display panel 20. Distilled water is used for rinsing the sample chamber between measurements of different samples.

A prototype of this PHASAR operates with a power consumption of about 55 milliamp and is capable of determining the concentration of AFFF in either fresh or sea water to a resolution of 0.01 percent by volume. That concentration is directly displayed by LED display 20. Most of the power consumption is by that LED digital display which draws currents on the order of 35 milliamp although this varies in response to the number and type of digits displayed. Both the power consumption and fluctuations created by the display unit could be reduced by using a low power liquid crystal display. In that type of design, the unit could satisfactorily be operated with a small lithium battery. Such units could even be solar powered given the efficiency of solar cells which are presently available.

Various modifications may be made to the preferred embodiment described above without departing from the spirit and scope of the invention as defined in the appended claims.

The embodiments of the invention in which an exclusive property or privilege is claimed are defined as follows:

1. A compact portable instrument for determining the percentage concentration of a material in a liquid solution comprising a refractive index sensor with a reflective type refractometer prism having a measuring surface located so that the measuring surface contacts any liquid in a sample holder and wherein the measuring surface of said prism is adjacent an outer side of the instrument, which outer side contains an inlet port for samples of liquid solution and an outlet port for that liquid; the measuring surface being separated from said outer side by a retainer plate having an opening therethrough, which opening extends around an exit from and an entrance to the inlet and exit ports respectively, with that measuring surface covering one side of said opening and wherein a liquid impervious seal exists around that opening between the retainer plate and the measuring surface and between the retainer plate and said outer side to form said sample holder; the instrument having a substantially monochromatic light source located at an entrance window to said prism, the light source upon activation directing a light beam at an angle towards said measuring surface where a portion of said beam is reflected by the prism to a photodetector at an exit window of the prism, the portion of beam reflected to the photodetector being dependent on a boundary formed by critical angle $\phi_{CRIT}$ at said measuring surface, which angle is dependent on refractive indices of the prism and any liquid in contact with the measuring surface, and wherein the refractive index of a liquid solution in contact with the measuring surface is dependent on the percentage concentration of material in that liquid; an output from the photodetector being connected to the instrument's display unit via at least one amplifier having a gain such that the percentage concentration of a material in the liquid being sampled is directly displayed by the display unit.

2. A compact portable instrument as defined in claim 1, wherein the entrance window and exit window of the prism are both located on one side of the prism adjacent to said measuring surface, the light source and photodetector being mounted on a circuit board that is securable to said one side by at least one fastening device, the circuit board being moveable parallel to said one side prior to being securely clamped to said one side by said fastening device so that the position of the photodetector and light source with respect to the location at which the light beam is reflected from the measuring surface and to the photodetector can be initially adjusted in order to optimize performance.

3. A compact portable instrument as defined in claim 1, wherein an output from said photodetector is applied to a − input of a first amplifier of a dual op-amp whose output is connected to the −input of a second amplifier of the dual op-amp whose output is connected to an input of the display unit and via a first potentiometer to the − input of that second amplifier, the first potentiometer providing a gain control for the dual op-amp to compensate for thin film fouling of the prism, a supply voltage being connected by a second potentiometer to the + input of the first amplifier, the second potentiometer providing an offset control to allow adjustment of the instrument to an initial "0" setting prior to any measurement of sample solutions.

4. A compact portable instrument as defined in claim 1, characterized in that an O-ring is located in said opening in said retainer plate which opening is oval shaped and snugly holds said O-ring in an oval shape, the inlet and exit ports being located at opposite ends of said oval shape with the O-ring surrounding their outer portions, a support structure for the prism pressing said measuring surface against the O-ring which is captured in said opening between the measuring surface and said outer side, said O-ring forming said liquid impervious seals.

5. A compact portable instrument as defined in claim 4, wherein the sample holder is ≦1 mm thick.

6. A compact portable instrument as defined in claim 4, wherein the entrance window and exit window of the prism are both located on one side of the prism adjacent to said measuring surface, the light source and photodetector being mounted on a circuit board that is securable to said one side by at least one fastening device, the circuit board being moveable parallel to said one side prior to being securely clamped to said one side by said fastening device so that the position of the photodetector and light source with respect to the location at which the light beam is reflected from the measuring surface and to the photodetector can be initially adjusted in order to optimize performance.

7. A compact portable instrument as defined in claim 4, wherein an output from said photodetector is applied to a − input of a first amplifier of a dual op-amp whose output is connected to the −input of a second amplifier of the dual op-amp whose output is connected to an input of the display unit and via a first potentiometer to the − input of that second amplifier, the first potentiometer providing a gain control for the dual op-amp to compensate for thin film fouling of the prism, a supply voltage being connected by a second potentiometer to the + input of the first amplifier, the second potentiometer providing an offset control to allow adjustment of the instrument to an initial "0" setting prior to any measurement of sample solutions.

8. A compact portable instrument as defined in claim 1, wherein the display unit has a digital display panel.

9. A compact portable instrument as defined in claim 2, wherein the display unit has a digital display panel.

10. A compact portable instrument as defined in claim 3, wherein the display unit has a digital display panel.

11. A compact portable instrument as defined in claim 6, wherein the display unit has a digital display panel.

12. A compact portable instrument as defined in claim 2 wherein the prism has a reflecting surface at an angle to the measuring surface, the light source being positioned to direct the beam towards said measuring surface where a portion of the beam is reflected onto said reflecting surface which reflects that portion towards said photodetector.

13. A compact portable instrument as defined in claim 4 wherein the sample holder has a volume ≦100 microliters.

14. A compact portable instrument invention for determining the percentage concentration of a material in a liquid solution comprises a refractive index sensor with a reflective type refractometer prism having a measuring surface that forms one wall of a sample holder and wherein a substantially monochromatic light source, when activated, directs a conical beam of light into the prism and towards a portion of the measuring surface which contacts any liquid solution in the sample holder, the measuring surface reflecting a portion of the beam which is directed towards a photodetector, that portion being dependent on a boundary formed by a critical angle $\phi_{CRIT}$ at the measuring surface; the instrument having a support for the prism and a retainer plate with an opening therethrough, said support pressing the measuring surface of said prism towards said retainer plate to press said plate towards an outer panel of said instrument with a waterproof seal being formed around said opening between the retainer plate and outer panel and between the retainer plate and said measuring surface, the outer panel having an inlet port and an outlet port which are surrounded by said opening whereby a liquid solution can be inserted into that opening through the input port and removed from that opening via said exit port, the opening forming said sample holder for liquid solutions whose refractive index can be determined by the reflected portion of the said beam detected by said photodetector where the refractive index provides an indication of a percentage concentration by volume of a material forming part of the liquid solution in the sample holder.

15. A compact portable instrument as defined in claim 14, wherein said opening is oval shaped with the inlet port being located at one end of the oval and the exit port located at another end of said oval, an O-ring being snugly fitted in said opening and held in an oval shape by edges of that opening, the waterproof seal being formed by said O-ring being compressed between the measuring surface and outer panel by pressure exerted on said prism by said support.

16. A compact portable instrument as defined in claim 15, wherein an output from said photodetector is applied to at least one amplifier whose output is connected to a digital display panel, said at least one amplifier having a gain that is adjustable and, with proper calibration, allows the percentage concentration to be directly displayed by said display panel.

17. A compact portable instrument as defined in claim 14, wherein an output from said photodetector is applied to a − input of a first amplifier of a dual op-amp whose output is connected to the −input of a second amplifier of the dual op-amp whose output is connected to an input of a display unit and via a first potentiometer to the − input of that second amplifier, the first potentiometer providing a gain control for the dual op-amp to compensate thin film fouling of the prism, a supply voltage being connected by a second potentiometer to the + input of the first amplifier, the second potentiometer providing an offset control to allow adjustment of the instrument to an initial "0" setting prior to any measurement of sample solutions.

18. A compact portable instrument as defined in claim 1, wherein the sample holder is ≦1 mm thick.

19. A compact portable instrument as defined in claim 15, wherein the sample holder has a volumn ≦100 microliters and is ≦1 mm thick.

20. A compact portable instrument as defined in claim 14, wherein the sample holder has a volumn ≦100 microliters and is ≦1 mm thick.

* * * * *